United States Patent [19]

Mayer

[11] 4,073,822

[45] * Feb. 14, 1978

[54] METHOD FOR CONTINUOUSLY CONTROLLING THE EQUIVALENT WATER CONTENT OF FLUOROSULFURIC ACID CATALYSTS

[75] Inventor: Ivan Mayer, Summit, N.J.

[73] Assignee: Exxon Research & Engineering Co., Linden, N.J.

[*] Notice: The portion of the term of this patent subsequent to Apr. 19, 1977, has been disclaimed.

[21] Appl. No.: 756,479

[22] Filed: Jan. 3, 1977

Related U.S. Application Data

[63] Continuation-in-part of Ser. No. 645,270, Dec. 29, 1975, Pat. No. 4,018,846.

[51] Int. Cl.² .............................................. C07C 3/54
[52] U.S. Cl. ........................... 260/683.47; 260/683.58
[58] Field of Search ..................... 260/683.47, 683.58, 260/683.59, 683.62

[56] References Cited

U.S. PATENT DOCUMENTS

| | | | |
|---|---|---|---|
| 2,592,063 | 4/1952 | Persyn, Jr. | 260/683.59 |
| 2,765,218 | 10/1956 | Amir | 260/683.59 |
| 3,173,969 | 3/1965 | Kapff | 260/683.59 |
| 3,513,220 | 5/1970 | Brandel | 260/683.59 |
| 3,625,655 | 12/1971 | Culp | 260/683.58 |
| 3,864,346 | 2/1975 | Child et al. | 260/683.59 |
| 3,887,635 | 6/1975 | Parker et al. | 260/683.47 |
| 4,018,846 | 4/1977 | Mayer | 260/683.59 |

*Primary Examiner*—George Crasanakis
*Attorney, Agent, or Firm*—John W. Ditsler

[57] ABSTRACT

The equivalent water content of hydrocarbon conversion catalyst comprising water and fluorosulfuric acid, i.e. the water equivalent to the water used to form the active catalyst, is determined continuously by contacting $SO_3$, e.g. fuming sulfuric acid, with said catalyst in a flow ratio sufficient to maintain the mixture thus formed at the point of incipient fuming. The presence of $SO_3$ evolved therefrom is determined by use of an $SO_3$ detector. The flow ratio at the point of incipient fuming is a direct measure of the equivalent water used to form the catalyst system. The equivalent water content thus measured is then compared to the desired equivalent water content and a signal corresponding to the deviation is used to vary the rate of fresh acid makeup, the rate of water addition, or both to the hydrocarbon conversion process reaction zone so as to maintain the desired equivalent water content of the catalyst therein.

9 Claims, 1 Drawing Figure

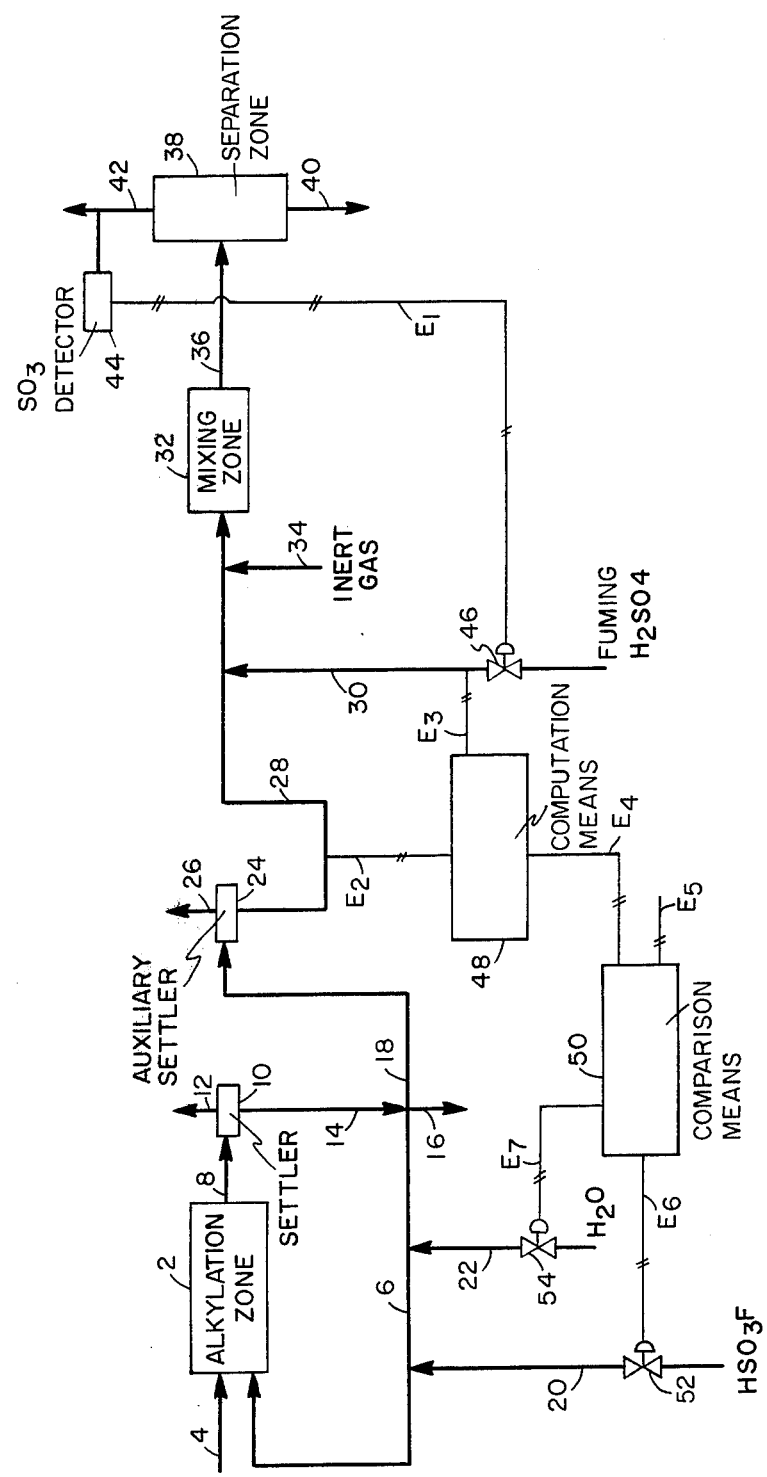

METHOD FOR CONTINUOUSLY CONTROLLING THE EQUIVALENT WATER CONTENT OF FLUOROSULFURIC ACID CATALYSTS

CROSS REFERENCE TO RELATED APPLICATIONS

This is a continuation-in-part of application Ser. No. 645,270 filed Dec. 29, 1975, now U.S. Patent 4,018,846.

BACKGROUND OF THE INVENTION

1. Field of the Invention

This invention relates to a method for controlling the equivalent water content of a catalyst stream comprising water and a strong acid. More specifically, this invention concerns a method for continuously monitoring the equivalent water content of a hydrocarbon conversion catalyst, particularly an alkylation catalyst, comprising water and fluorosulfuric acid by adding $SO_3$, e.g. fuming sulfuric acid, to a sample of said catalyst at a rate sufficient to maintain the mixture thus formed at the point of incipient fuming and detecting the presence of the $SO_3$ evolved therefrom. The equivalent water content of the catalyst sample can then be determined from the flow rate of the sample and the flow rate and composition of the fuming sulfuric acid. The equivalent water content of the catalyst stream being monitored can then be controlled by regulating the addition rate of fresh acid, water or both to the hydrocarbon conversion process in accordance with the deviation between the equivalent water content and the desired equivalent water content of the catalyst sample.

2. Description of the Prior Art

The alkylation of paraffins with olefins in the presence of a catalyst comprising fluorosulfuric acid is well known in the petroleum refining art, see, for example, in U.S. Pat. No. 3,887,635, the disclosures of which are incorporated herein by reference. Typically, in such processes a paraffin, preferably an isoparaffin such as isobutane, and olefins such as butenes are alkylated in the presence of a catalyst formed from fluorosulfuric acid and water according to the following equation:

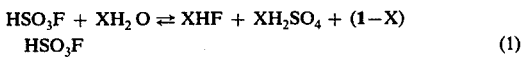

$$HSO_3F + XH_2O \rightleftharpoons XHF + XH_2SO_4 + (1-X)HSO_3F \quad (1)$$

where X represents the moles of water per mole of fluorosulfuric acid employed to form the catalyst. The water serves to produce a catalyst of reduced acidity vis-a-vis the fluorosulfuric acid, and thereby decreases the probability of undesirable competing side reactions which have a detrimental effect on product quality, while increasing catalyst selectivity to desirable highly branched paraffinic products to form alkylate product of high quality. Since the composition of the active catalyst and the selectivity of same will depend upon the amount of water employed, it would be desirable to have available simple and convenient method of determining the water equivalent to that used to form the desired catalyst.

A method has been suggested for determining the water content of a sulfuric acid catalyst in which fuming sulfuric acid is mixed with the acid catalyst until fuming is initiated (see Albright, L. F. et al, "Alkylation of Isobutane with Butenes; Effect of Sulfuric Acid Compositions," Ind. Eng. Chem. Process Des. Devlop. Vol. II (No. 3), p. 446–450, 1972). However, it is believed that this method does not suggest controlling continuously the equivalent water content of a fluorosulfuric acid catalyst as is described herein below.

SUMMARY OF THE INVENTION

Now according to the present invention, it has been found that the equivalent water content of hydrocarbon conversion catalyst, particularly an alkylation catalyst, comprising water and fluorosulfuric acid can be controlled continuously by intimately contacting a sample of said acid catalyst with $SO_3$, e.g. a stream of fuming sulfuric acid, and sensing the presence of the $SO_3$ thus formed. A signal from an $SO_3$ detector is developed in accordance with the sensed conditions such that the addition rate of fuming sulfuric acid to the acid catalyst stream is maintained at the point of incipient fuming; i.e. the point at which $SO_3$ is first evolved from the catalyst-fuming sulfuric acid mixture. The equivalent water content of the acid catalyst stream can be determined from the chemistry and stoichiometry of the reactions, the flow ratio of the two acid streams and the free $SO_3$ concentration of the fuming sulfuric acid stream, i.e. the $SO_3$ in the fuming sulfuric acid that is not chemically combined as $H_2SO_4$. A control signal is developed in accordance with the equivalent water content thus determined and coordinated with a signal corresponding to the desired water content. The control signal is then applied to a control means which regulates the addition rate of fresh acid, of water or both to the alkylation process so as to control the equivalent water content of the acid catalyst employed in said process. The acid catalyst stream referred to herein may be a catalyst stream employed at any point in the alkylation process; e.g. fresh, intermediate or spent acid catalyst.

BRIEF DESCRIPTION OF THE DRAWING

The single FIGURE is a block diagram illustrating the control system of the present invention applied to a typical alkylation process.

DESCRIPTION OF THE PREFERRED EMBODIMENT

Having thus described the invention in general terms, reference is now made to the FIGURE which shows one embodiment of the present invention for a spent fluorosulfuric acid alkylation catalyst. Such details are included as are necessary for a clear understanding of how the present invention may be applied to controlling the water content of said acid catalyst. No intention is made to unduly limit the scope of the present invention to the particular configuration shows as variations obvious to those having ordinary skill in the art of controlling alkylation processes are included within the broad scope of the present invention.

Referring now to the FIGURE, there is shown a portion of an alkylation process in which a paraffin is reacted with olefins in a reaction zone in the presence of a catalyst comprising water and fluorosulfuric acid to form a reaction product having a higher molecular weight than that of the paraffinic reactant or those products formed by self-alkylation. The reaction product is normally a mixture of $C_5$–$C_{14}$ saturates, often termed "alkylate," and typically contains a mixture of $C_7$–$C_9$ hydrocarbons, the specific composition of which depends upon the particular paraffinic and olefinic reactants and the operating conditions utilized.

Suitable olefinic reactants includes $C_2$–$C_{12}$ terminal and internal monoolefins such as ethylene, propylene, isobutylene, butene-1, butene-2, the pentenes (e.g., trimethylethylene) and similar higher monoolefinic hydrocarbons of either a straight chain or a branched chain structure. Preferably, the $C_2-C_6$ monoolefins are used, although the highly-branched $C_7-C_{12}$ monoolefins may also be used. The reaction mixtures may also contain small amounts of diolefins and other type hydrocarbons normally present in refinery hydrocarbon streams. Although it is desirable from an economic standpoint to use the normally gaseous olefins as reactants, normally liquid olefins may be used. Thus, reactable polymers, copolymers, interpolymers, crosspolymers, and the like, of the above-mentioned olefins, such as, for example, the diisobutylene and triisobutylene polymers, the codimer of normal butylene and isobutylene of butadiene and isobutylene, may be employed as an olefinic reactant. Mixtures of two or more of the olefins described above can be used as the process feedstock.

$C_2$, $C_3$, $C_4$ and/or $C_5$ olefin cuts from thermal and/or catalytic cracking units; field butanes which have been subjected to prior isomerization and/or partial dehydrogenation treatment; refinery stabilizer bottoms; spend gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried to control excess water buildup, i.e. about 5 to 15 wppm or less of water, before entering the alkylation zone.

The paraffinic feedstocks that can be reacted with the olefins desirably comprise straight and/or branched chain $C_4-C_{10}$ paraffins such as hexane, butane and the like, and preferably $C_4-C_6$ isoparaffins such as isobutane, isopentane, isohexane and the like. While open chain hydrocarbons are preferred, cycloparaffins such as methylcyclopentane may also be used.

As shown in the FIGURE, the paraffin and olefins enter alkylation reaction zone 2 via line 4 and contact a recycle acid stream introduced via line 6. The olefin stream is, preferably, admixed with a paraffin before introducing the combined stream into reaction zone 2. If desired, however, the olefin and paraffin streams can be fed directly into reaction zone 2. The olefin concentration in the feed ranges from 0.5 to 25 volume percent or greater based on total feed and preferably below 10 volume percent. Translated into volume rations, high volume ratios of paraffin to olefin ranging from about 10:1 to 200:1 or higher are preferred, although somewhat lower ratios may be used, e.g., 3:1. Correspondingly high volume ratios of paraffin to olefin are also desired within the alkylation zone. Preferably, the paraffin/olefin ratio therein ranges from about 5:1 to 2,000:1 or higher.

The hydrocarbon-spent acid (spent catalyst) mixture formed in alkylation zone 2, often referred to as an "emulsion mixture," is then passed via line 8 to emulsion settler 10 wherein said mixture is separated from the spend acid. The hydrocarbon product is then discharged from settler 10 via line 12 and passed to additional separation facilities (not shown), e.g., fractionation zone, for recovery of the alkylate and recycle paraffin. The spend acid catalyst is removed from settler 10 via line 14 and a major portion thereof is recycled to alkylation zone 2 via line 6. A small portion of the acid catalyst not recycled to the alkylation zone is purged from the system via line 16. A sample of the acid catalyst is shown leaving settler 10 via line 18. As an example of the relative magnitudes of streams 6, 14, 16 and 18, if 25,000 B/D of acid catalyst is discharged from settler 10 via line 14, typically from about 100 to about 300 B/D of acid catalyst would be withdrawn via line 16 while less than 50, preferably less than 20, more preferably less than 10 and tuypically from about 1-5 B/D would be removed via line 18. The remaining acid catalyst would be recycled to reaction zone 2 via line 6. Fresh fluorosulfuric acid makeup and water are shown being added to recycle acid stream 6 via lines 20 and 22, respectfully, to maintain the desired catalyst inventory and composition in alkylation zone 2 as will be described further hereinbelow. The fresh fluorosulfuric acid makeup and water may be added to the system as shown in the FIGURE or at any convenient location in the recycle loop following emulsion settler 10 or, if desired, directly to well-mixed reaction zone 2.

The spent acid calalyst from settler 10 may contain small amounts of hydrocarbons that were not mechanically separated in settler 10. Such hydrocarbons will significantly affect the specific gravity of the spent acid catalyst stream in line 18 which can cause erroneous flow meter readings (for orifice type, i.e. pressure drop, meters) and hence false readings regarding the amount of equivalent water present in said stream. Therefore, the spent acid catalyst present in line 18 is passed to an auxiliary emulsion settler 24 to effect the substantial removal of entrained hydrocarbons from the catalyst. The hydrocarbons thus removed leave settler 24 via line 26 and a substantially hydrocarbon-free spent acid is discharged, preferably at a constant flow rate, via line 28. By substantially hydrocarbon-free is meant that the acid catalyst contains less than 1%, preferably less than 0.1%, mechanically separable hydrocarbons based on acid catalyst. The auxiliary emulsion settler 24 is operated at substantially the same temperature as emulsion settler 10.

The substantially hydrocarbon-free spent acid catalyst sample is then contacted with $SO_3$, e.g. fuming sulfuric acid which is introduced into the system via line 30. Such fuming sulfuric acid is a readily available article of commerce. Preferably, the fuming sulfuric acid employed comprises from about 102 to about 105 wt.% sulfuric acid. When the fuming sulfuric acid is contacted with the catalyst sample, the free $SO_3$ in the fuming sulfuric acid may undergo the following reactions depending upon the amount of water present in the original catalyst; i.e. whether "X" in equation (1) is less than, equal to or greater than 1:

$$HF + SO_3 \rightarrow HSO_3F \qquad (2)$$

$$H_2O + SO_3 \rightarrow H_2SO_4 \qquad (3)$$

For example, when $X < 1$, say 0.5, equation (1) may be written as

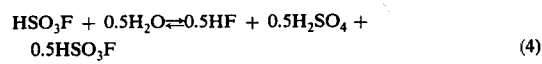

$$HSO_3F + 0.5H_2O \rightleftharpoons 0.5HF + 0.5H_2SO_4 + 0.5HSO_3F \qquad (4)$$

When $X=1$, equation (1) becomes
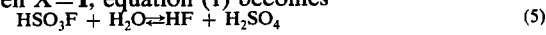
$$HSO_3F + H_2O \rightleftharpoons HF + H_2SO_4 \qquad (5)$$

In equations (4) and (5), once substantially all of the HF has been reacted with $SO_3$ according to equation (2), $SO_3$ will be evolved from the catalyst-fuming sulfuric acid mixture. Similarly, when $X > 1$, say 10, equation (1) becomes

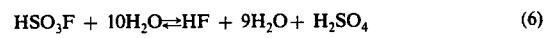

$$HSO_3F + 10H_2O \rightleftharpoons HF + 9H_2O + H_2SO_4 \qquad (6)$$

In equation (6), once substantially all of the HF and H$_2$O have reacted with SO$_3$ according to equations (2) and (3) [to give one equivalent water via equation (2) and nine equivalent waters via equation (3)], SO$_3$ will be evolved from the catalyst-fuming sulfuric acid mixture.

By the stoichiometry of the particular reaction, e.g. equations (4)–(6), the point of incipient fuming corresponds to the water equivalent to the total water added to the fluorosulfuric acid to form the original catalyst, i.e., the equivalent water. Typically, the mixture fumes when it comprises from 100 to about 100.2 wt.% sulfuric acid.

The above discussion assumes that no HF is added to or removed from the alkylation reaction system. For example, if excess HF is added to the original catalyst (i.e., more than is required to form the desired catalyst), the equivalent water and the excess HF is measured. The addition of H$_2$SO$_4$ acid does not affect the above reactions, per se. However, it may be desired to maintain a particular mole ratio of H$_2$SO$_4$ to HF in the catalyst, i.e. a mole ratio other than one.

The amount of fuming sulfuric acid added relative to the spent acid catalyst present in line 28 depends upon the flow rate of said acid catalyst and the amount of HF, water or mixtures thereof present therein, as well as the concentration of free SO$_3$ in the fuming sulfuric acid added to the system. For example, if a 100 gm per unit time spent acid sample containing 20 wt.% free HF, 30 wt.% H$_2$SO$_4$, 40 wt.% HSO$_3$F, and 10 wt.% carbonaceous material that is normally formed during the alkylation process, is intimately contacted with a stream of fuming sulfuric acid containing 103.15 wt.% sulfuric acid (14 wt.% free SO$_3$), the amount of fuming sulfuric acid required to cause fuming according to equations (2) and (3) assuming the fuming starts at 100 wt.% acid, is about 571.4 gr (~301.5 cc). Therefore, each 0.1 wt.% water expressed as wt.% free HF in the spent acid requires the addition of about 1.5 cc (about 2.9 gms) per unit time of the 103.15 wt.% fuming sulfuric acid to produce fuming of the mixture. It should be pointed out that the stronger the fuming sulfuric acid, the less than need be added. However, more accurate control is possible by use of weaker fuming acid.

The spent acid catalyst-fuming sulfuric acid mixture is then passed into a mixing zone 32 to provide a substantially uniform mixture of the two acid streams to ensure that the SO$_2$ present in the fuming sulfuric acid will have reacted with the HF, water or mixtures thereof in the spent acid according to equations (2) and (3). The mixing can be accomplished in any convenient manner provided the acid streams are intimately mixed. Examples of suitable mixing means include a series of orifice mixers, mechanical stirrers, and the like. If orifice mixers are employed, it is preferred to have at least six in series with a total pressure drop of at least 15 psi.

It is desirable, although not necessary to the practice of the present invention, that an inert gas such as nitrogen be contacted with the spent acid catalyst-fuming sulfuric acid mixture prior to entering the mixing chamber 32 to facilitate release of sufficient gas phase to enable subsequent detection of SO$_3$. The gas can be any gas that is inert to the spend acid catalyst-fuming sulfuric acid mixture. The amount of inert gas added, e.g. via line 34, is not critical provided it is sufficient to facilitate the release of a major portion of the excess SO$_3$ from the acid mixture, i.e. a major portion of the excess free SO$_3$ equivalent to the wt.% H$_2$SO$_4$ and fluorosulfuric acid above 100 is stripped from the acid mixture. For example, if the mixture is 100.1% H$_2$SO$_4$ plus HSO$_3$F and if the stripped acid mixture will contain about 100.02 wt.% H$_2$SO$_4$ (based on carbonaceous complex-free catalyst), about 80% of the SO$_3$ will be released from the mixture due to introduction of the inert gas. Preferably, the flow ratio of inert gas to the catayst sample should be maintained substantially constant to obtain about the same relative degree of stripping.

The substantially uniform mixture is then passed via line 36 into separation zone 38 wherein said mixture is separated into a gas phase and an acid mixture phase. The acid mixture phase comprises fluorosulfuric acid catalyst and is discharged from separation zone 38 via line 40. The gas phase comprises traces of SO$_3$, inert gas as well as any small quantities of volatile hydrocarbon not removed in auxiliary emulsion settler 10. Although it is desirable that the acid catalyst-fuming sulfuric acid mixture be maintained at the point of incipient fuming, it is possible that SO$_3$ may not be present in the vapor stream since more HF and/or H$_2$O may be present relative to the SO$_3$ being added such that substantially all of the free SO$_3$ is reacted with the HF and/or H$_2$O. Small amounts of dissolved SO$_3$ may also be present in the acid mixture phase. The separation zone may be any suitable apparatus for separating vapor and liquid mixtures. Internal packing and trays are not required provided the separation zone is designed to comprise sufficient cross-sectional area and disengaging height above the liquid level to prevent the presence of entrained liquid in the gas phase.

The gas phase is then discharged from separation zone 38 via line 42 and a portion thereof introduced into SO$_3$, detector 44 which senses the presence of SO$_3$ therein. The detector can be any suitable apparatus for sensing SO$_3$ continuously. One example of such an apparatus is described in Oil and Gas Journal, Vol. 66, p. 89, Apr. 15, 1968, the disclosures of which are incorporated herein by reference. A control signal E1 from the SO$_3$ detector is developed in accordance with the sensed conditions such that the addition rate of fuming sulfuric acid via line 30 to the acid catalyst sample in line 28 is maintained at the point of incipient fuming, i.e. the point where SO$_3$ is first evolved from the spent acid catalyst-fuming sulfuric acid mixture above a threshold level resulting from the partial pressure of SO$_3$ at the operating conditions. Typically, this threshold level is less than 0.1 mm of mercury for the fluorosulfuric acid catalyst systems. The control signal E1 is then transmitted to control means 46 which regulates the flow rate of fuming sulfuric acid such that the presence of SO$_3$ in the gas phase 42 is maintained at substantially incipient conditions. A control signal E2 corresponding to the flow rate of the acid catalyst sample and a control signal E3 corresponding to the flow rate and the free SO$_3$ concentration of fuming sulfuric stream 30 are then introduced into computation means 48 which calculates by material balance, according to the chemistry, i.e. the stoichiometry, of the reactions shown in equations (1)–(3), depending on the value of "X" as illustrated in equations (4)–(6), the amount of equivalent water present in the stream 28. Suitable computation means can be selected from a variety of digital or analog computing devices, depending upon the particular application. For example, the computation means could be a large computer capable of controlling an entire refinery complex or, if desired, a minicomputer designed for more limited applications. Such computation means are well known articles of commerce and thus are readily available in the marketplace.

The equivalent water content thus calculated is then developed into a control signal E4 and sent to a comparison means 50 which compares signal E4 with a signal E5 corresponding to the desired equivalent water content of the acid catalyst stream being monitored such that a control signal E6 is generated. The control signal E6 is then applied to control means 52 which regulates the addition rate of fresh fluorosulfuric acid of known concentration to maintain the desired equivalent water content in the acid catalyst stream being monitored. Alternatively, a control signal E7 could be generated in comparison means 50 and then applied to control means 54 which regulates the water addition rate to alkylation zone 2. Hence, the desired equivalent water content in the catalyst stream being monitored can be maintained by regulating the addition rate of fresh fluorosulfuric acid, water or both.

Thus, according to the present invention, when the HF and/or water present in the fluorosulfuric acid catalyst sample contacts the fuming sulfuric acid containing free $SO_3$, the HF and/or $H_2O$ and free $SO_3$ react according to equations (2)-(3) above until substantially all of the HF and/or $H_2O$ is reacted. The presence of $SO_3$ above the threshold value is then sensed by the $SO_3$ detector causing the addition rate of the fuming sulfuric acid to be varied such that the acid catalyst-fuming sulfuric acid mixture will be maintained at the point of incipient fuming. The water content of the catalyst sample can then be determined by material balance from the chemistry of the reaction (equation (1) depending on the value of "X") knowing the flow rate of the sample, and the flow rate and free $SO_3$ concentration of the fuming sulfuric acid. Thus, the control system described herein seeks to maintain the acid mixture at the point of incipient fuming to enable determination of the equivalent water content of the acid catalyst. The calculated (actual) equivalent water content of the sample of the catalyst stream being monitored is then compared with the desired equivalent water content and the addition rate of fresh acid, water or mixtures thereof is controlled such that the desired equivalent water content will be obtained in a selected period of time. A change in the equivalent water content of the catalyst sample will cause a change in the $SO_3$ sensed which will in turn effect a change in the addition rate of the fuming sulfuric acid such that a new equivalent water content will be calculated. As before, the newly calculated equivalent water content will then be compared with the desired value such that the addition rate of fresh acid, water or mixtures thereof will be adjusted to match the desired equivalent water content in the selected period of time. By using the present invention, the water content of the acid stream can be maintained within plus or minus 1%, preferably within plus or minus 0.5 wt.%, and more preferably within plus or minus 0.2 wt.%, based on acid catalyst, of the desired value.

The temperature of the present invention may also range broadly but should be maintained at a level sufficient to avoid freezing of an acid stream at any point in the system. Thus, the temperature should be maintained above the melting point of the acid stream at any point in the system, be it fuming sulfuric acid stream, the acid stream being monitored or a mixture of the two. In general, the present invention should be operated at a pressure sufficiently low to avoid the evolution, at the particular temperature of the system, of light hydrocarbons dissolved in the catalyst, e.g., isobutane, from the acid stream being monitored.

Control means (e.g. valve means), sensing means (e.g. flow orifices), comparison means (e.g. conventional digital or analog controllers), the means for obtaining the catalyst sample (e.g. a probe), and the like equipment are well known articles of commerce and, as such, are readily available from various vendors.

What is claimed is:

1. In an alkylation process wherein a paraffin is reacted with olefins in the presence of an acid catalyst formed from at least fluorosulfuric acid and water according to the reaction

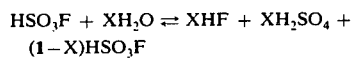

$$(1-X)HSO_3F$$

where X is the moles of water per mole of fluorosulfuric acid, to provide an acid catalyst-hydrocarbon mixture to a settling zone wherein a hydrocarbon product is separated from the acid catalyst, a major portion of the acid catalyst from said settling zone is being recycled to the alkylation zone, and wherein fresh fluorosulfuric acid, water or mixtures of said fluorosulfuric acid and water are added to said alkylation process, the improvement which comprises continuously controlling the equivalent water content of said acid catalyst by continuously controlling the addition rate of fresh fluorosulfuric acid, water or mixtures thereof to said alkylation process, according, to the steps:

1. withdrawing a sample of the acid catalyst from said settling zone;
2. intimately contacting said sample with a stream of fuming sulfuric acid in an amount sufficient to ensure substantially complete reaction of the HF present in said sample with the $SO_3$ present in said fuming sulfuric acid when $X \leq 1$ and to ensure substantially complete reaction of the HF, water or mixtures of said HF and water present in said sample when $X > 1$;
3. sensing the presence of $SO_3$ evolved in step (2) after said complete reaction of the HF, water or mixtures of said HF and water present in said sample and providing a control signal in accordane with said sensed presence of $SO_3$;
4. controlling the rate of fuming sulfuric acid addition in step (2) in response to the control signal of step (3) such that said concentrated acid in step (2) is at the point of incipient fuming;
5. sensing the flow rate of the sample being withdrawn in step (1) and the flow rate of said fuming sulfuric acid stream being added in step (2);
6. providing a signal corresponding to the equivalent water content of the sample of step (1) in accordance with the sensed flow rate of said sample and the flow rate of said fuming sulfuric acid of step (5);
7. providing a reference signal in a computation means corresponding to a desired equivalent water content in said acid catalyst;
8. comparing the signals from step (6) and step (7) to provide a control signal;
9. controlling the addition rate of fresh fluorosulfuric acid, water or mixtures of said fluorosulfuric acid and water to said process in accordance with the control signal from step (8) and thereby controlling the equivalent water content of the acid catalyst during said alkylation.

2. The process of claim 1 wherein the equivalent water content of the acid catalyst is maintained within plus or minus 1 wt.%, based on acid catalyst, of said desired equivalent water content.

3. The process of claim 2 wherein the equivalent water content of the acid catalyst is maintaind within plus or minus 0.5 wt.%, based on acid catalyst, of said desired equivalent water content.

4. The process of claim 1 wherein the contacting of step (2) is effected in the presence of an inert gas.

5. The process of claim 4 wherein the inert gas is nitrogen.

6. The process of claim 1 wherein the concentrated acid from step (2) is separated into a gas phase comprising $SO_3$ and a liquid catalyst phase comprising said acid.

7. The process of claim 1 wherein the acid catalyst of step (1) contains less than 1 wt.% mechanically separable hydrocabons based on acid catalyst.

8. The process of claim 1 wherein the paraffin is an isoparaffin.

9. The process of claim 1 wherein HF additional to that formed according to said reaction is added to said acid catalyst in said alkyation zone.

* * * * *

UNITED STATES PATENT OFFICE
CERTIFICATE OF CORRECTION

PATENT NO. : 4,073,822
DATED : February 14, 1978
INVENTOR(S) : Ivan Mayer

It is certified that error appears in the above-identified patent and that said Letters Patent are hereby corrected as shown below:

On page 1, after "[*] Notice:" the recitation "The portion..... disclaimed" should be deleted and replaced by --The portion of the term of this patent subsequent to April 19, 1994, has been disclaimed--.
At column 4, in equation (3), delete "S0₃" and insert in place thereof --SO₃--.
At column 5, line 42, delete "than" and insert in place thereof --that--.
At column 8, line 45, delete "accordane" and insert in place thereof --accordance--.
At column 9, line 6, delete "maintaind" and insert in place thereof --maintained--.

Signed and Sealed this

Sixth Day of June 1978

[SEAL]

Attest:

RUTH C. MASON
Attesting Officer

DONALD W. BANNER
Commissioner of Patents and Trademarks